United States Patent
Lindblad et al.

(10) Patent No.: US 10,538,473 B2
(45) Date of Patent: Jan. 21, 2020

(54) METHOD FOR CATALYTIC CONVERSION OF KETOACIDS AND HYDROTREAMENT TO HYDROCARBONS

(71) Applicant: NESTE OYJ, Espoo (FI)

(72) Inventors: Marina Lindblad, Helsinki (FI); Elias Ikonen, Espoo (FI); Maaria Seläntaus, Helsinki (FI); Mats Käldström, Porvoo (FI)

(73) Assignee: NESTE OYJ, Espoo (FI)

( * ) Notice: Subject to any disclaimer, the term of this patent is extended or adjusted under 35 U.S.C. 154(b) by 35 days.

(21) Appl. No.: 15/276,350

(22) Filed: Sep. 26, 2016

(65) Prior Publication Data

US 2017/0008864 A1  Jan. 12, 2017
US 2018/0009731 A9  Jan. 11, 2018

Related U.S. Application Data

(63) Continuation of application No. PCT/EP2015/056655, filed on Mar. 26, 2015.

(30) Foreign Application Priority Data

Mar. 26, 2014 (EP) ..................................... 14161793
Dec. 22, 2014 (EP) ..................................... 14199725

(51) Int. Cl.

| | | |
|---|---|---|
| *C07C 51/00* | (2006.01) | |
| *C07C 51/353* | (2006.01) | |
| *C10G 50/00* | (2006.01) | |
| *C10L 1/06* | (2006.01) | |
| *C10G 3/00* | (2006.01) | |
| *B01J 35/10* | (2006.01) | |
| *C10L 1/08* | (2006.01) | |
| *B01J 23/10* | (2006.01) | |
| *B01J 23/30* | (2006.01) | |
| *B01J 35/00* | (2006.01) | |
| *C07C 51/367* | (2006.01) | |
| *C07D 307/33* | (2006.01) | |
| *C07C 59/347* | (2006.01) | |
| *B01J 21/04* | (2006.01) | |
| *B01J 21/06* | (2006.01) | |
| *B01J 23/04* | (2006.01) | |
| *B01J 23/883* | (2006.01) | |
| *C10L 1/04* | (2006.01) | |
| *B01J 23/00* | (2006.01) | |
| *B01J 21/08* | (2006.01) | |

(52) U.S. Cl.
CPC ............ *C07C 51/353* (2013.01); *B01J 21/04* (2013.01); *B01J 21/063* (2013.01); *B01J 23/04* (2013.01); *B01J 23/10* (2013.01); *B01J 23/30* (2013.01); *B01J 23/883* (2013.01); *B01J 35/002* (2013.01); *B01J 35/1014* (2013.01); *B01J 35/1019* (2013.01); *C07C 51/367* (2013.01); *C07C 59/347* (2013.01); *C07D 307/33* (2013.01); *C10G 3/46* (2013.01); *C10G 3/47* (2013.01); *C10G 3/48* (2013.01); *C10G 3/50* (2013.01); *C10G 50/00* (2013.01); *C10L 1/04* (2013.01); *C10L 1/06* (2013.01); *C10L 1/08* (2013.01); *B01J 21/08* (2013.01); *B01J 23/002* (2013.01); *B01J 35/10* (2013.01); *C10G 2300/202* (2013.01); *C10G 2300/301* (2013.01); *C10G 2300/302* (2013.01); *C10G 2300/304* (2013.01); *C10G 2400/02* (2013.01); *C10G 2400/04* (2013.01); *C10G 2400/08* (2013.01); *C10L 2200/0469* (2013.01); *C10L 2270/04* (2013.01); *Y02P 30/20* (2015.11)

(58) Field of Classification Search
CPC ...................................................... B01J 35/1019
USPC ......................................................... 562/508
See application file for complete search history.

(56) References Cited

U.S. PATENT DOCUMENTS

| | | | |
|---|---|---|---|
| 2,440,751 | A | 5/1948 | Legatski |
| 5,254,794 | A | 10/1993 | Wu |
| 5,345,026 | A | 9/1994 | Chang et al. |
| 5,382,731 | A | 1/1995 | Chang et al. |
| 5,608,105 | A | 3/1997 | Fitzpatrick |
| 6,206,940 | B1 | 3/2001 | Weissman et al. |
| 8,003,818 | B2 | 8/2011 | Van Den Brink et al. |
| 8,362,306 | B2 | 1/2013 | Wheeler et al. |
| 8,629,310 | B2 | 1/2014 | Lotero et al. |
| 2006/0135793 | A1 | 6/2006 | Blessing et al. |
| 2006/0162239 | A1 | 7/2006 | Van Den Brink et al. |

(Continued)

FOREIGN PATENT DOCUMENTS

| | | |
|---|---|---|
| CN | 101993739 A | 3/2011 |
| CN | 102676201 A | 9/2012 |

(Continued)

OTHER PUBLICATIONS

Snell, R.W.; Shanks, B.H. "CeMOx-Promoted Ketonization of Biomass-Derived Carboxylic Acids in the Condensed Phase"; ACS Catalysis (published 2013), 4, 512-518.*

(Continued)

*Primary Examiner* — Sharon Pregler
(74) *Attorney, Agent, or Firm* — Buchanan Ingersoll & Rooney PC

(57) ABSTRACT

Catalytic conversion of ketoacids is disclosed, including methods for increasing the molecular weight of ketoacids. An exemlary method includes providing in a reactor a feedstock having at least one ketoacid. The feedstock is then subjected to one or more C—C-coupling reaction(s) in the presence of a catalyst system having a first metal oxide and a second metal oxide.

26 Claims, 3 Drawing Sheets

(56) References Cited

U.S. PATENT DOCUMENTS

| | | | |
|---|---|---|---|
| 2011/0098503 A1 | 4/2011 | Wheeler et al. | |
| 2012/0095275 A1* | 4/2012 | Coleman | C07C 2/36 585/329 |
| 2012/0209037 A1 | 8/2012 | Viljoen et al. | |
| 2012/0323053 A1* | 12/2012 | Qiao | C10G 1/06 568/959 |
| 2013/0079566 A1* | 3/2013 | Lin | C07C 51/21 585/242 |
| 2013/0237728 A1* | 9/2013 | Lotero | C10L 1/04 585/242 |
| 2015/0018581 A1 | 1/2015 | Kettunen et al. | |
| 2015/0018588 A1 | 1/2015 | Myllyoja et al. | |

FOREIGN PATENT DOCUMENTS

| | | |
|---|---|---|
| GB | 601922 A | 5/1948 |
| GB | 762136 A | 11/1956 |
| WO | WO 95/03262 A1 | 2/1995 |
| WO | WO 00/47697 A1 | 8/2000 |
| WO | WO 2006/056591 A1 | 6/2006 |
| WO | WO 2006/067171 A1 | 6/2006 |
| WO | WO 2011/053584 A1 | 5/2011 |
| WO | WO 2013/113976 A1 | 8/2013 |

OTHER PUBLICATIONS

Gaertner, C.A.; Serrano-Ruiz, J.C.; Braden, D.J.; Dumesic, J.A. "Catalytic coupling of carboxylic acids by ketonization as a processing step in biomass conversion", Journal of Catalysis (2009), 266, 71-78.*

International Search Report (PCT/ISA/210) dated Jul. 3, 2015, by the Finnish Patent Office as the International Searching Authority for International Application No. PCT/FI2015/050208.

International Search Report (PCT/ISA/210) dated Aug. 13, 2015, by the Finnish Patent Office as the International Searching Authority for International Application No. PCT/FI2015/050209.

International Search Report (PCT/ISA/210) dated Aug. 24, 2015, by the European Patent Office as the International Searching Authority for International Application No. PCT/EP2015/056655.

Office Action dated Nov. 23, 2017, by the State Intellectual Property Office (SIPO) of the People's Republic of China in corresponding Chinese Patent Application No. 201580016498.3. (7 pages).

Second Office Action dated Jul. 31, 2018, by the State Intellectual Property Office (SIPO) of the People's Republic of China in corresponding Chinese Patent Application No. 201580016498.3. (7 pages).

Third Office Action dated Mar. 27, 2019, by the Chinese Patent Office in corresponding Chinese Patent Application No. 201580016498.3, and an English Translation of the Office Action. (8 pages).

* cited by examiner

Figure 1 – Conversion of lignocellulosic material to levulinic acid
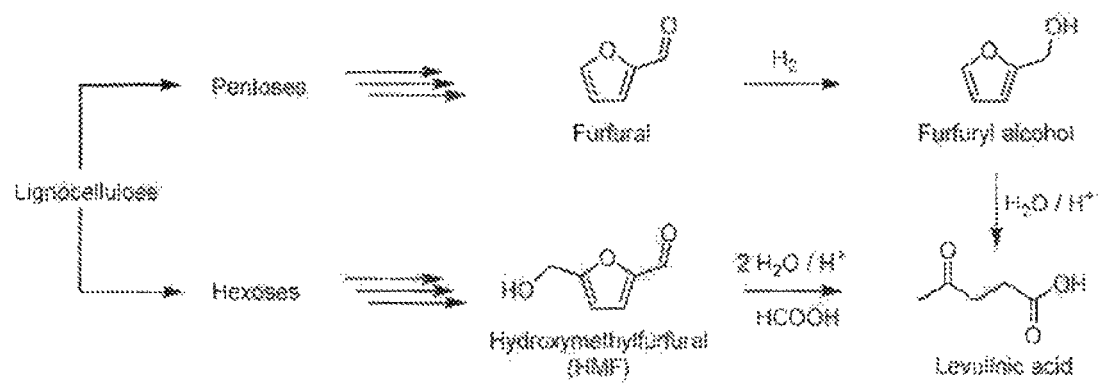
Figure 2 – Reaction products of levulinic acid
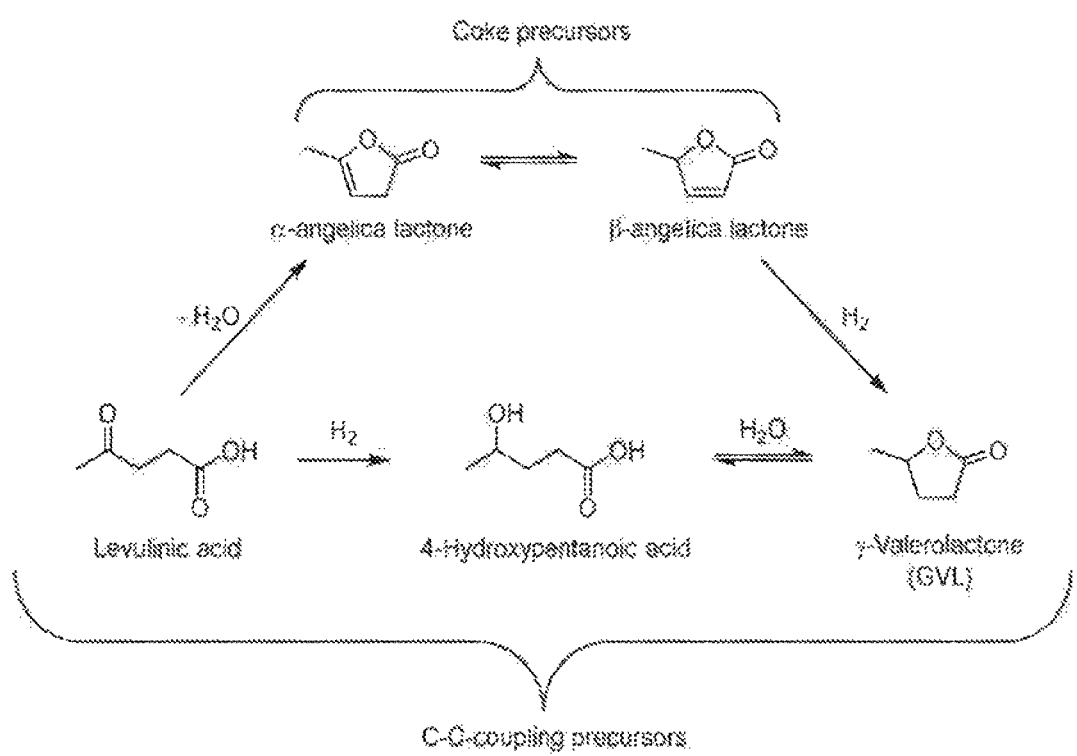

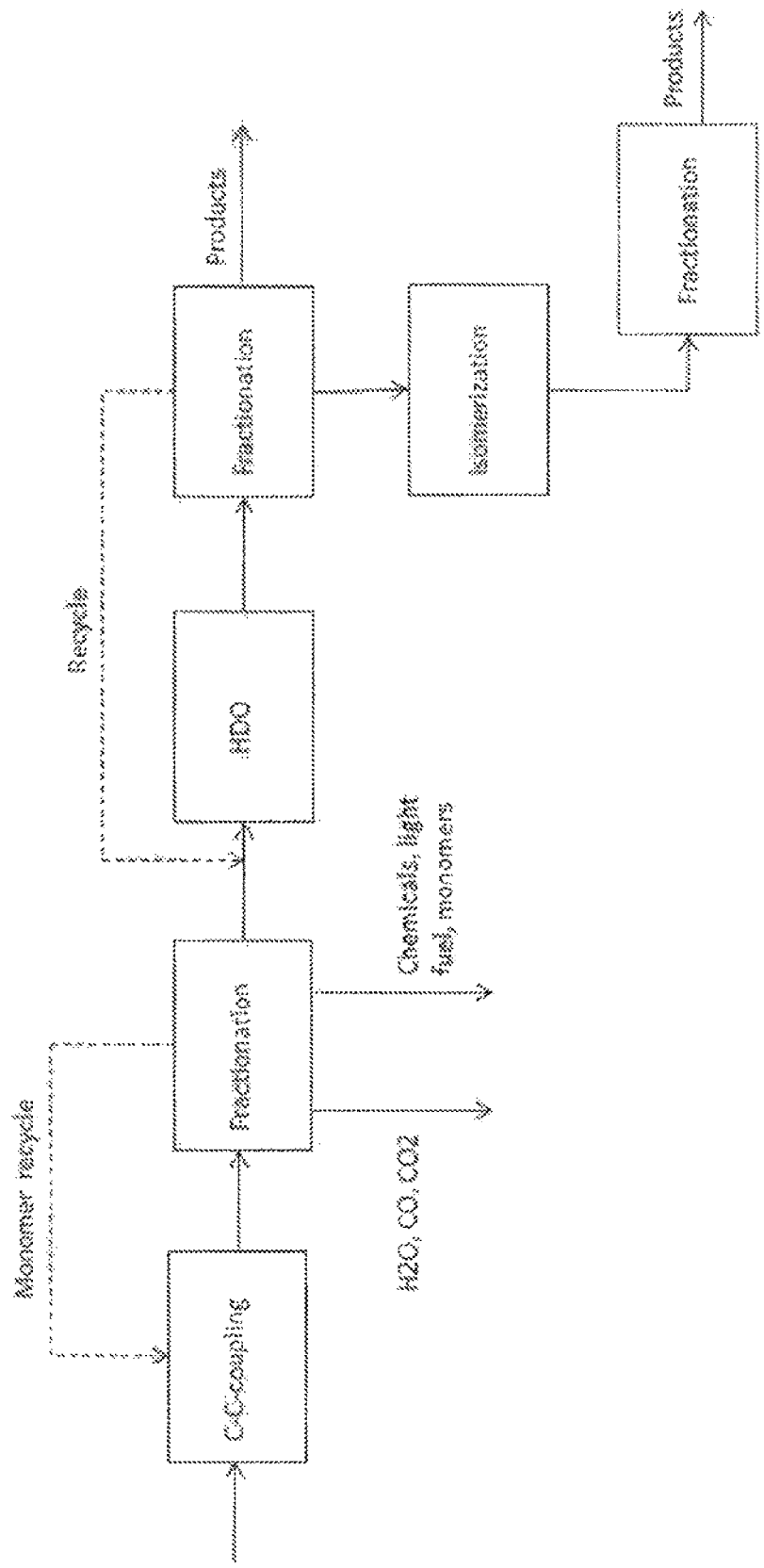

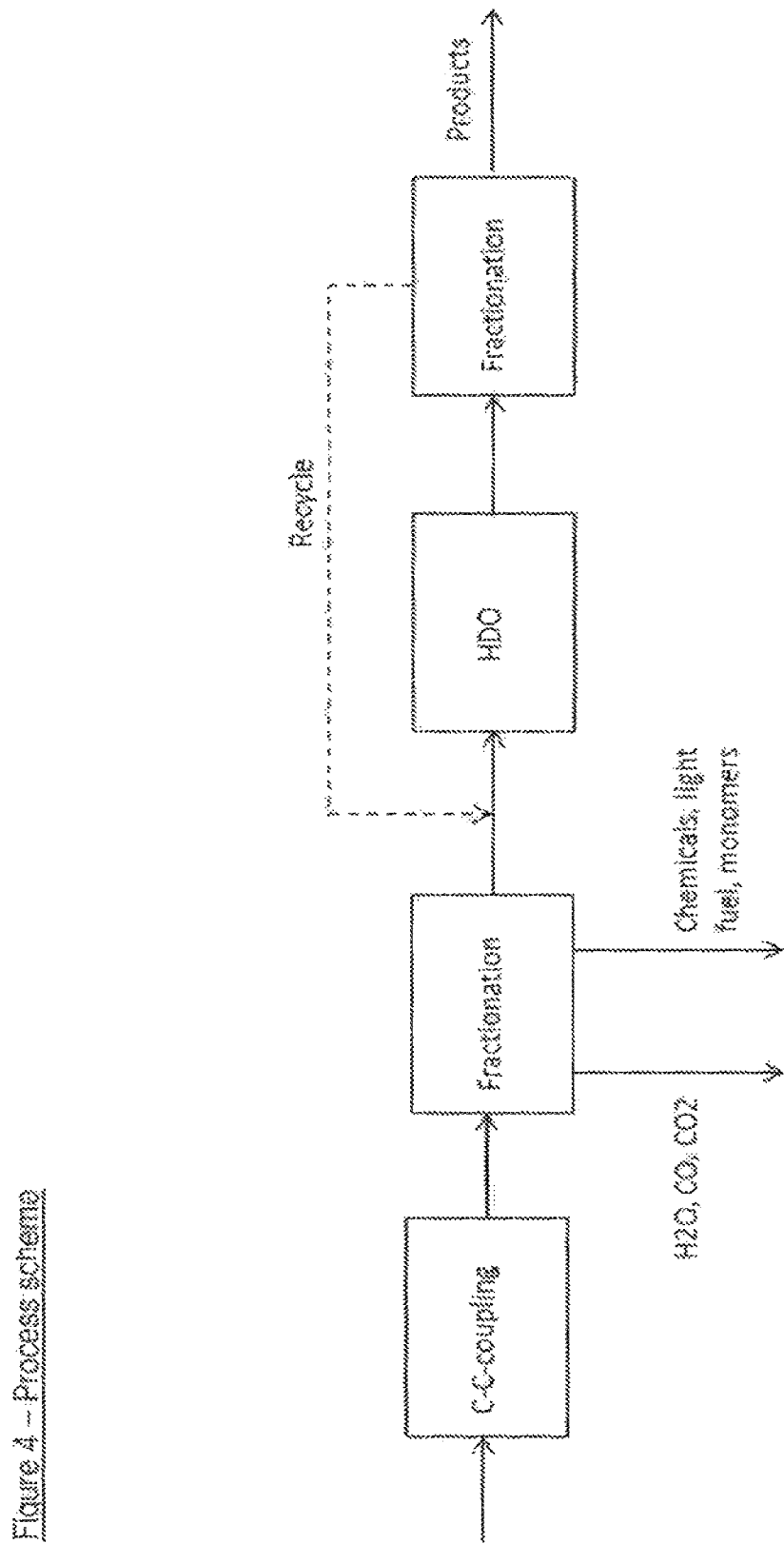
Figure 3 – Process scheme

METHOD FOR CATALYTIC CONVERSION OF KETOACIDS AND HYDROTREAMENT TO HYDROCARBONS

RELATED APPLICATIONS

This application claims priority as a continuation application under 35 U.S.C. § 120 to PCT/EP2015/056655, which was filed as an International Application on Mar. 26, 2015 designating the U.S., and which claims priority to European Application 14161793.6 filed in Europe on Mar. 26, 2014 and which claims priority to European Application 14199725.4 filed in Europe on Dec. 22, 2014. The entire contents of these applications are hereby incorporated by reference in their entireties.

FIELD

The present disclosure relates to catalytic conversion of ketoacids, including methods for increasing the molecular weight of ketoacids, products obtainable by such methods, as well as use of such products for the production of liquid hydrocarbons and/or gasoline or diesel fuel or base oil components.

BACKGROUND INFORMATION

Production of hydrocarbons used as fuel or base oil components and chemicals from biomass are of increasing interests since they are produced from a sustainable source of organic compounds.

The ketoacid Levulinic acid (LA, 4-oxopentanoic acid) is one of many platform molecules that may be derived from biomass. It may be produced from both pentoses and hexoses of lignocellulosic material (see FIG. 1) at relatively low cost. Levulinic acid as a platform molecule is considered to be a reactive molecule due to both its keto and acid functionality.

Esters of levulinic acid have been suggested as fuel components as well as cold flow additives in diesel fuels, and for example, the methyl and ethyl esters have been used as additives in diesel fuel. Gamma-valerolactone (GVL), which may be obtained by reduction of levulinic acid, has been used as a fuel additive in gasoline. Further reduction of GVL to 2-methyltetrahydrofuran (MTHF) provides a product that may be blended with gasoline of up to 60%. Alkyl valerates produced from levulinic acid have also been suggested as biofuels.

Levulinic acid has also been used for the production of liquid hydrocarbon fuels by a number of catalytic routes, including a method of producing a distribution of alkenes, the distribution centered around $C_{12}$, involving converting aqueous GVL in a first reactor system to butenes followed by oligomerization in a second reactor over an acidic catalyst (e.g. Amberlyst® 70).

Serrano-Ruiz et al. (*Appl. Catal., B*, 2010, 100, 184) produced a $C_9$-ketone (5-nonanone) by reducing levulinic acid to GVL over a Ru/C catalyst in one reactor followed by reacting 40 wt % GVL in water and 0.02 M $H_2SO_4$ in a $Pd/Nb_2O_5$+ceria-zirconia double bed arrangement at 325-425° C., 14 bar, WHSV=0.8-0.5 $h^{-1}$ in another reactor. Using multiple reactors can offer more control over the process compared to using a single reactor. However, multiple reactors increase the number of process steps, which increases the capital expenditure of the process.

US Patent Publication No. 2006/0135793 A1 (to Blessing and Petrus) discloses dimerization of levulinic acid to a $C_{10}$ unit in the presence of hydrogen, with a strong acidic heterogenous catalyst, e.g., ion exchange resin catalyst, having a hydrogenating metal, at a temperature in the range from 60 to 170° C. and a pressure of 1 to 200 bar (absolute). The example indicates as main products levulinic acid dimers (26%) and unreacted levulinic acid (70%). Relatively low reaction temperatures can be preferred due to the thermal instability of ion exchange resins at temperatures of above 150° C.

SUMMARY

A method is disclosed for increasing the molecular weight of a ketoacid, the method comprising: providing in a reactor a feedstock having at least one ketoacid; and subjecting the feedstock to one or more C—C-coupling reaction(s), wherein the C—C-coupling reaction(s) are conducted in a presence of a solid acid catalyst system having a first metal oxide and a second metal oxide, and wherein a content of the at least one ketoacid in the feedstock is at least 30 wt-%.

A method is also disclosed for producing hydrocarbons by increasing a molecular weight of a ketoacid to obtain a C—C-coupling reaction product: providing in a reactor a feedstock having at least one ketoacid; subjecting the feedstock to one or more C—C-coupling reaction(s), wherein the C—C-coupling reaction(s) are conducted in a presence of a solid acid catalyst system having a first metal oxide and a second metal oxide, and wherein a content of the at least one ketoacid in the feedstock is at least 30 wt-%; and subjecting the C—C-coupling reaction product to hydrodeoxygenation.

A hydrocarbon composition is disclosed, comprising: at least 30 wt-% paraffins; at least 50 wt-% naphthenes; less than 10 wt-% aromatics; and wherein at least 70 wt-% of the hydrocarbons have a carbon number from 8 to 10.

A hydrocarbon composition is also disclosed, comprising: at least 60 wt-% aliphatic hydrocarbons; and at least 30 wt-% aromatics; and wherein at least 70 wt-% of the hydrocarbons have a carbon number from 9 to 24.

BRIEF DESCRIPTION OF THE DRAWINGS

Other features and advantages of the present disclosure will become apparent to those skilled in the art upon reading the detailed description of the embodiments in conjunction with the accompanying drawings, wherein:

FIG. 1 shows a scheme illustrating exemplary conversion of lignocellulosic material to levulinic acid;

FIG. 2 shows a scheme illustrating exemplary reaction products of levulinic acid, including potential coke precursors and potential C—C-coupling precursors; the figure is not intended to cover all reaction products of levulinic acid, nor is it intended to show all types of coke precursors; FIG. 2 illustrates one exemplary mechanism for reducing angelica lactone coke precursors by hydrogenation, and also illustrates that the intermolecular ester of 4-hydroxypentanoic acid, GVL, may be in equilibrium with 4-hydroxypentanoic acid itself;

FIG. 3 shows an overview of an exemplary process scheme for upgrading products from the C—C-coupling reactions; and FIG. 4 shows an overview of an exemplary process scheme for preparing and upgrading the products from the C—C-coupling reactions.

DETAILED DESCRIPTION

Using a single reactor compared to multiple reactors may be advantageous in that this can reduce a number of process steps and increase process economy. Some drawbacks associated with direct routes of upgrading (e.g., by using single reactors) are that these reactions generate highly reactive intermediates with more than one functional group, which can further react to other undesired molecules. Reduction of undesired molecules by direct routes of upgrading can entail a lower yield of a desired product composition. The suppression of side reactions producing undesired molecules can be accomplished by using dilute aqueous solutions of levulinic acid as feedstock. Accordingly, an indirect route of upgrading a feedstock using multiple reactors or multiple catalyst beds in a single reactor may in some situations be desirable to a direct route of upgrading.

Additional processes for upgrading levulinic acid and other ketoacids to higher molecular weight compounds are therefore disclosed, which are suitable as, for example, fuel or base oil components or chemicals or as components in the production of fuel or base oil components or chemicals. For example, additional processes are disclosed, which reduce the processing costs by, for example, improving the yield of the desired components or chemicals, and/or reduce the overall catalyst consumption by improving the life time of the catalyst.

The present disclosure was made to, for example, to provide methods that enable upgrading of ketoacids such as levulinic acid to higher molecular weight compounds.

Exemplary embodiments provide the upgrade of ketoacids to higher molecular weight compounds in good yield and at low processing costs.

An exemplary method for increasing the molecular weight of a ketoacid, includes providing in a reactor a feedstock having at least one ketoacid, and subjecting the feedstock to one or more C—C-coupling reaction(s), wherein the C—C-coupling reaction(s) are conducted in the presence of a solid acid catalyst system having a first metal oxide and a second metal oxide, and wherein the content of the at least one ketoacid in the feedstock is at least 30 wt-%.

In subjecting the feedstock to one or more C—C-coupling reaction(s), the at least one ketoacid undergoes at least one C—C-coupling reaction with another ketoacid or ketoacid derivative present in the feedstock so as to increase the molecular weight of the ketoacid. The ketoacids participating in the C—C-coupling reaction may be of the same type having the same chemical formula or of a different type. The ketoacid derivate includes all compounds directly obtainable from the ketoacid through C—C-coupling reactions or other reactions. The ketoacid derivatives may be selected from the list including (e.g., consisting of) lactones and lactone derivatives of ketoacids, and pentanoic acid.

In a C—C-coupling reaction the at least one ketoacid reacts with another reactant with the formation of a new carbon-carbon bond in the product. In other words, the molecular weight of the ketoacid is increased using the ketoacid as a direct precursor (one-step reaction) and within a single reactor or a single catalyst bed. As a matter of course, further C—C-coupling reactions may occur so as to further increase the molecular weight the C—C-coupling reaction product. These further reactions are conducted in the same (single) reactor or catalyst bed.

That is, the inventors of the present disclosure in a first aspect found that a solid acid catalyst system having a first metal oxide and a second metal oxide catalyses multiple types of C—C-coupling reactions of ketoacids in a strong solution (at least 30 wt-%) of ketoacids enabling the production of higher molecular weight compounds of ketoacids at a good yield and in a reactor.

Using strong solutions of ketoacids allows for high probability of C—C-coupling reactions between two ketoacids, thus providing a high yield of desired products and low amounts of side-products. The solvent of the (strong) solution may be any ketoacid, such as the "at least one ketoacid". In addition, water and/or organic solvents may be used. For example, the at least one ketoacid acts as a solvent.

The catalyst system can have a specific surface area of from 10 to 500 m$^2$/g. The specific surface can be determined by the BET method, which measures the adsorption isotherm of nitrogen (ASTM D-3663).

The catalyst system can have a total amount of acid sites in the range of 30 and 500 μmol/g. The total number of acid sites can be measured with NH3-TPD method, which is a known method for determining the number of acid sites and has been disclosed e.g. in M. Lashdaf et al, Microporous and Mesoporous Materials 75 (2004) 149-158. In the NH3-TPD method, adsorption temperature of NH3 of 200° C. is used.

In the present disclosure, the at least one ketoacid is for example a γ-ketoacid, most preferably for example levulinic acid. In addition to the at least one ketoacid, one or more further ketoacids may be employed.

The reactor employed in the method as disclosed may be a flow reactor, such as a continuous flow reactor, or a batch reactor, preferably under stirring. A flow reactor type can be preferred from the viewpoint of production efficiency. When using a flow reactor, the catalyst system is for example immobilized in the reactor.

A method is disclosed for industrial scale production of higher molecular weight products of ketoacids and, therefore, the C—C-coupling reactions are conducted using a feedstock having a high concentration of ketoacids. For example, the content of the at least one ketoacid in the feedstock is at least 40 wt-%, preferably at least 50 wt-%, more preferably at least 70 wt-%, even more preferably at least 90 wt-%, and even more preferably at least 95 wt-%. If multiple ketoacids are present in the feedstock, the "content of the at least one ketoacid" refers to the total content of all ketoacids.

In this respect, it is to be noted that the term "feedstock" in the present disclosure includes all material fed to the reactor except for the material constituting the catalyst system. Thus, the calculation of the content of the at least one ketoacid in the feedstock does not consider the amount of catalyst.

Water has been found to decrease the formation of coke precursors during the C—C-coupling reactions but it has been also found to decrease the activity of catalyst system. The content of water in the feedstock is for example, less than 5.0 wt-%, and more preferably less than 2.0 wt-% and even more preferably less than 1.0 wt-%. The calculation of the content of water in the feedstock does not consider the amount of catalyst.

There are several metal oxides which can be used in the catalyst system to catalyse the C—C-coupling reactions of ketoacids. For example, the first metal oxide includes an oxide of one of W, Be, B, Mg, Si, Ca, Sc, Ti, V, Cr, Mn, Fe, Co, Ni, Cu, Zn, Ga, Sr, Y, Zr, Nb, Mo, Cd, Sn, Sb, Bi, La, Ce, Th and the second metal oxide includes an oxide of one of Zr, Ti, Si, Al, V, Cr or a combination of these, the first metal oxide not being same as second metal oxide. Combinations of metal oxides include mixtures of individual metal oxides (solid solutions), mixed metal oxides and supported metal oxides.

The catalyst system can include a mixture of the first metal oxide and the second metal oxide, wherein the second metal oxide is at least one selected from zirconia, titania, silica, vanadium oxide, chromium oxide, preferably for example, zirconia or titania.

In the present disclosure, the mixture of metal oxides includes a mixture of individual metal oxide materials, (e.g. in a powder form) mixed metal oxides, where the metal oxides form a common matrix, and supported metal oxides, where the more active metal oxide is deposited on the metal oxide acting as a carrier.

Various methods can be used for the preparation of mixtures of metal oxides. In preparation of mixed metal oxides, metal oxide precursors are brought together from gas phase or liquid solution before transformation into oxide form. In preparation of supported metal oxides, a metal oxide precursor is brought from gas phase or liquid solution onto a solid support in oxide (or hydroxide) form before the transformation of the metal oxide precursor into oxide form.

The first metal oxide can be supported on a second metal oxide carrier, wherein the second metal oxide is for example selected from the group including (e.g., consisting of) zirconia, titania, silica, vanadium oxide, chromium oxide, preferably for example, zirconia or titania.

The surface density of metal atoms of the first metal oxide supported on the second metal oxide can, for example, be from 0.5 to 20 metal atoms/nm$^2$. The surface density of metal atoms of the first metal oxide in the catalyst system is calculated based on the content of metal oxide in the catalyst and specific surface area of the catalyst system.

The catalyst system can include tungsten oxide, ceria or silica supported on a metal oxide carrier, wherein the carrier is for example, selected from the group consisting of zirconia, titania, silica, vanadium oxide, chromium oxide, preferably zirconia or titania. A carrier constituted of multiple oxides selected from the above second metal oxides may be employed as well.

The first metal oxide is tungsten oxide, ceria or silica and the content of the first metal oxide in the catalyst system can, for example, be 1.0 to 40.0 wt-%, preferably 2.0 to 30.0 wt-%, further preferably 13.0 to 30.0 wt-%, calculated by weight of the metal oxide in relation to the total mass of the catalyst. The metal oxide content is determined by measuring the metal content in the catalyst and calculating the content of the metal oxide in which the metal is present in the highest oxidation number, if multiple (stable) oxides of one metal exist.

The feedstock can be introduced into the reactor in liquid phase, as opposed to for example the gaseous phase. One of the exemplary advantages of introducing the feedstock into the reactor in the liquid phase is that it is not required to heat the feedstock to prepare a gaseous stream. Further, the presence of solid components in the feedstock may lead to clogging of the catalyst. Therefore, the feedstock can be in liquid phase and does not include a considerable amount of solid material, e.g. less than 4.0 wt-%, preferably less than 1.0 wt-%, more preferably less than 0.2 wt-% of solid material. Here, solid material includes solid material suspended or dispersed in a liquid phase.

The C—C-coupling reaction(s) can be controlled by adjusting several parameters, including by selection of reaction conditions such as: temperature, pressure, and weight hourly space velocity (WHSV) (kg feedstock/kg catalyst per hour).

The C—C-coupling reaction(s) are for example, conducted at a temperature of 200-350° C., preferably 210-300° C., more preferably 220-280° C. and even more preferably 220-260° C. This temperature range was found to be particularly suitable for obtaining a high degree of reaction products of medium molecular weight (C8-C25) while avoiding excessive polymerization and coking of the catalyst.

The C—C-coupling reaction(s) can be conducted at a pressure of 0.5-100 bar, preferably 1.0-50 bar, more preferably 1.0-20 bar.

The C—C-coupling reactions can be conducted at a weight hourly space velocity of for example, 0.05 h$^{-1}$ to 2.0 h$^{-1}$, preferably 0.1 h$^{-1}$ to 1.8 h$^{-1}$, more preferably 0.2 h$^{-1}$ to 1.5 h$^{-1}$, most preferably 0.25 h$^{-1}$ to 1.25 h$^{-1}$. The WHSV has an influence on the composition of the resulting material, since it determines the effective contact time of reagent and catalyst. The above-mentioned ranges have shown to provide a high degree of favourable products.

The C—C-coupling reaction(s) may be conducted in the presence of hydrogen. In this case, the hydrogen is fed to the reactor as part of the feedstock, either simultaneously with the remainder of the feedstock, or introduced via a separate inlet within the reactor.

It is also possible to conduct the C—C-coupling reaction(s) in the absence of hydrogen and to recover the catalyst by adding hydrogen to the reaction or in the course of a wash step mixture from time to time.

The C—C-coupling reactions may be conducted at a feed ratio (H2/liquid feedstock) of, for example,100-3000 Nl/l, preferably 200-2000 Nl/l, more preferably 500-1800 Nl/l and most preferably 500-1500 Nl/l. Here the liquid feedstock refers to feedstock, which is predominantly in liquid form at the reaction conditions.

If the C—C-coupling reaction(s) may be conducted in the presence of hydrogen, the catalyst system may also include at least one hydrogenation metal selected from Group VIII of the Periodic Table of Elements, preferably from Co, Ni, Ru, Rh, Pd, and Pt.

In a further aspect of the present disclosure, C—C-coupling reaction products obtainable by the methods disclosed herein are disclosed.

In another aspect of the present disclosure, methods for producing hydrocarbons from a feedstock having at least one ketoacid are disclosed.

In still another aspect of the present disclosure, hydrocarbon compositions obtainable by the methods according to the present disclosure are disclosed.

One of the challenges in increasing the molecular weight of ketoacids by C—C-coupling reactions is the high reactivity of the product intermediates, which results in too high a degree of oligomerisation of the starting components.

The inventors have found that the oligomerisation of a ketoacid, specifically of levulinic acid, in the presence of a solid base catalyst such as $K_2O/TiO_2$ results in high formation of coke and tar, which poison the catalyst by inhibiting the reactive sites on the surface of the catalyst and eventually result in plugging of the reactor. Without being bound to any theory this is suggested to occur due to reactions of levulinic acid to more reactive precursors such as angelica lactones, which are known to have a high tendency to polymerise at temperatures of over 200° C.

It was attempted to reduce the undesired polymerization reactions and to control the oligomerization reactions and coking by conducting the reactions in dilute aqueous solutions. The addition of water to suppress coking reactions was, however, found also to decrease the performance of the base catalyst resulting in low yields of the desired oligomerization products.

The embodiments disclosed herein are based on a surprising finding that the molecular weight of ketoacids can be selectively increased by subjecting the ketoacids to C—C- coupling reactions in the presence of a solid acid catalyst system having a first metal oxide and a second metal oxide. The use of a solid acid catalyst system having first and second metal oxides has been found to suppress the coking tendency of the reaction intermediates and simultaneously to catalyze multiple types of C—C-coupling reactions resulting in formation of new carbon-carbon bonds between the reactants in solutions.

An exemplary method is disclosed for increasing the molecular weight of a ketoacid, the method comprising providing in a reactor a feedstock having at least one ketoacid, and subjecting the feedstock to one or more C—C-coupling reaction(s), wherein the C—C-coupling reaction(s) are conducted in the presence of a solid acid catalyst system having a first metal oxide and a second metal oxide and wherein a content of the at least one ketoacid in the feedstock is at least 30 wt-%.

The present disclosure also presents methods for increasing the molecular weight of ketoacids.

Ketoacids are organic molecules that have both a keto function (>C═O) as well as a carboxylic acid (COOH) or carboxylate (COO⁻) function. In the present specification special forms of ketoacids include embodiments where the keto function is an aldehyde (—CH═O).

In the present disclosure, the ketoacid may for example be an alpha-ketoacid (such as pyruvic acid, oxaloacetic acid and alpha-ketoglutaric acid), beta-ketoacid (such as acetoacetic acid), gamma-ketoacid (such as levulinic acid), or delta-ketoacid. The ketoacid may have more than one keto functionality, and more than one carboxylic acid function. For example, the ketoacid only has one keto functionality and one carboxylic acid functionality.

Scheme 1

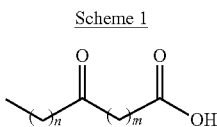

Scheme 1 illustrates exemplary ketoacids according to the present disclosure, wherein n, for example, and m are integers each selected independently of each other from the list consisting of 0, 1, 2, 3, 4, 5, 6, 7, 8, 9, 10. For example, the ketoacid is a gamma ketoacid, preferably levulinic acid (m=2, n=0).

The molecular weight of the ketoacids in the feedstock can be increased by at least 40% or more. For example, the molecular weight is increased to be from 150 to 1000 g/mol, such as 160 to 500 g/mol. Where the ketoacid is a C4-C7-ketoacid, the molecular weight may be increased to corresponding molecules having a C7-C35 carbon chain, such as a C8-C30 carbon chain.

For example, it can be preferable that more than 50 wt % of the reaction product belong to the group containing dimerization, trimerisation, tetramerisation, pentamerisation, and hexamerisation products of ketoacid. By dimerization, trimerisation, tetramerisation, pentamerisation and hexamerisation products is meant reaction products relating to two, three, four, five and six molecules of one or more of ketoacids being coupled together. In the case of a feedstock having, derivatives of ketoacids in addition to ketoacids, the dimerization, trimerisation, tetramerisation, pentamerisation, and hexamerisation products may additionally contain mixed C—C-coupling products having one or more ketoacids and/or derivatives thereof. The dimerisation, trimerisation, tetramerisation, pentamerisation, and hexamerisation products are derived from at least one ketoacid, such as at least two ketoacids, at least three ketoacids, at least four ketoacid, at least five ketoacids, at least six ketoacids.

In the present disclosure the molecular weight of the keto acids are increased through one or more C—C-coupling reaction(s). Many C—C-coupling reactions are known in the art, and those skilled in the art would be able to identify such C—C-coupling reactions based on the reaction conditions provided. For example, the C—C-coupling reactions may be ketonisation reactions or reactions proceeding through an enol or enolate intermediate. In the present disclosure, the C—C-coupling reactions may be selected from the list comprising: aldol-type reactions and condensations, ketonisations, reactions where the C—C-coupling involves an alkene, as well as other oligomerisation reactions. The C—C-coupling reactions may proceed with two identical types of molecules (i.e. the same compound) or may be a crossed reaction between two different types of molecules (i.e. between different compounds).

The reactivity of the catalyst depends on the number of active sites on the surface of the catalyst and on the specific surface of the catalyst. For example, the catalyst system has a specific surface area of from 10 to 500 m²/g. The catalyst system having a specific surface area in these ranges have shown to provide enough reactivity to obtain high yield of desired C—C-coupling reaction products such as dimers, trimers, tetramers, pentamers and hexamers of a ketoacid but at the same time to minimize the reactions of ketoacids to coke precursors.

The reactivity of a solid acid catalyst system depends also on the total amount of acid sites, which is for example in the range of 30 and 500 μmol/g.

The feedstock can include as the major component one or more ketoacids. For example, the content of the at least one ketoacid in the feedstock is at least 40 wt-% such as at least 50 wt-%, at least 70 wt-%, at least 90 wt-%, or at least 95 wt-%.

The content of water in the feedstock can, for example, be less than 5.0 wt-%, preferably less than 2.0 wt-%, more preferably less than 1.0 wt-%. Preferably, no water is present in the feedstock. Nevertheless, internal water may be produced in some condensation reactions.

The conversion of ketoacid to desired C—C-coupling reaction products was found to increase as the content of ketoacid in the feedstock increased. Presence of water was found to decrease the reactions of levulinic acid to coke precursors but addition of water also decreased catalyst activity and the yield of desired C—C-coupling reaction products was lowered. The yield of C—C-coupling products has to be high enough to enable an economically feasible process for production of fuel components and chemicals from ketoacids.

The feedstock may be obtained from processing of lignocellulosic material, and such processed material may be used directly, or purified to varying degrees before being used as a feedstock in the method of the present disclosure. The levulinic acid may be produced for example, with the Biofine method disclosed in U.S. Pat. No. 5,608,105, the disclosure of which is hereby incorporated by reference in its entirety.

The feedstock can include levulinic acid and the levulinic acid may be combined with one or more other ketoacids or derivatives of ketoacids.

The ketoacid derivatives may be selected from the list including (e.g., consisting of) lactones and lactone derivatives of ketoacids, and pentanoic acid.

The feedstock may include a mixture of levulinic acid in combination with ketoacid derivatives, such as at least 30 wt-% of levulinic acid and at least 10 wt-% of levulinic acid derivative(s) based on the total mass of feedstock.

In addition to ketoacids and ketoacid derivatives, the feedstock may also contain aldehydes, such as furfural or hydroxymethylfurfural.

Preferably the first metal oxide of the catalyst system used in the embodiments disclosed herein can, for example, include an oxide of one of W, Be, B, Mg, Si, Ca, Sc, Ti, V, Cr, Mn, Fe, Co, Ni, Cu, Zn, Ga, Sr, Y, Zr, Nb, Mo, Cd, Sn, Sb, Bi, La, Ce, Th and the second metal oxide includes, for example, an oxide of one of Zr, Ti, Si, Al, V, Cr or a combination of these, the first metal oxide not being same as second metal oxide. Combinations of metal oxides include solid mixtures of metal oxide materials, mixed metal oxides and supported metal oxides.

The catalyst system can include a mixture of the first metal oxide and the second metal oxide, wherein the second metal oxide is, for example, at least one selected from zirconia, titania, silica, vanadium oxide, chromium oxide, preferably zirconia or titania.

The catalyst system may include, for example, a mixture of tungsten oxide, ceria or silica and at least one oxide selected from zirconia, titania, silica, vanadium oxide, chromium oxide, preferably zirconia or titania.

The catalyst system can include, for example, tungsten oxide, ceria or silica supported on a metal oxide carrier, wherein the carrier is selected from the group consisting of zirconia, titania, silica, vanadium oxide, chromium oxide, preferably zirconia or titania. Here, the tungsten, cerium or silicon oxides represent the metal oxides having higher activity. These oxides have shown to provide good reaction properties. Furthermore, the carriers mentioned above have shown to provide good carrier properties without affecting the function of the more active part, including a synergistic interaction. Moreover, the combinations mentioned above allow using the catalyst for a long period of time without deterioration and/or dissolution in the acidic reaction medium and thus allow for reduced overall catalyst consumption.

The content of the first metal oxide in the catalyst system can, for example, be 1.0 to 40.0 wt-%, preferably 2.0 to 30.0 wt-%, further preferably 13.0 to 30.0 wt-%, calculated by weight of the metal oxide relative to the total mass of the catalyst.

The feedstock can be provided in a single reactor, or single reactor bed. The reactor should be able to be pressurized, and accommodate the feedstock and the catalyst system. The reactor should have means, such as one or more inlets and/or outlets, for supplying gases and adding/withdrawing feedstock. In addition, means for controlling the pressure and temperature can be present.

The feedstock can for example, be introduced into the reactor in liquid phase, as opposed to for example the gaseous phase. One of the advantages of introducing the feedstock into the reactor in the liquid phase is that it is not required to heat the feedstock to prepare a gaseous stream. Further, the presence of solid components in the feedstock may lead to clogging of the catalyst. Therefore, it can be preferable that the feedstock is in liquid phase and does not include a considerable amount of solid material (e.g., less than 4.0 wt-%, preferably less than 1.0 wt-%, more preferably less than 0.2 wt-% of solid material). Here, solid material includes solid material dispersed or suspended in a liquid phase.

The C—C-coupling reaction(s) are conducted predominantly in the liquid phase, as opposed to the gaseous phase, meaning that the reaction is at least predominantly taking place on the catalyst in the liquid phase. The C—C-coupling reaction(s) may be conducted entirely in the liquid phase.

The inventors found that the C—C coupling reaction(s) can be controlled by adjusting several parameters, including appropriate selection of reaction conditions such as: temperature, pressure, and weight hourly space velocity (WHSV) and reaction time/residence time.

The reaction temperature has been found to have a significant effect on the product distribution. At temperatures below 200° C. the yield of C—C-coupling products may be too low and at temperatures above 400° C. the yield may be decreased due to formation coke and other non-desired polymerization products. The C—C-coupling reaction(s) are for example conducted at a temperature of 200-400° C., preferably 210-300° C., more preferably 220-280° C. and even more preferably 220-260° C. The above cited temperature ranges were found to be particularly suitable for obtaining a high degree of reaction products of medium molecular weight (C8-C30) while avoiding excessive polymerization and coking of the catalyst.

Since most of the C—C-coupling reactions take place in liquid phase the pressure and temperature are suitably selected to keep the reactants in liquid phase. Advantageously, the C—C-coupling reaction(s) are conducted at a pressure of, for example, 0.5-100 bar, preferably 1.0-50 bar, more preferably 1.0-20 bar.

The C—C-coupling reactions are for example conducted at a weight hourly space velocity (kg feedstock/kg catalyst*hour) of 0.05 $h^{-1}$ to 2.0 $h^{-1}$, preferably 0.1 $h^{-1}$ to 1.8 $h^{-1}$, more preferably 0.2 $h^{-1}$ to 1.5 $h^{-1}$, most preferably 0.25 $h^{-1}$ to 1.25 $h^{-1}$. The WHSV has an influence on the composition of the resulting material, since it determines the effective contact time of reagent and catalyst. The above-mentioned ranges have shown to provide a high degree of favourable products.

The C—C coupling reaction(s) may proceed in the presence of hydrogen which is fed into the reactor as part of the feedstock. The hydrogen may be mixed with one or more other gasses, such as an inert gas such as nitrogen, argon, helium or another of the noble gasses, or gas behaving inertly to the reaction conditions of the present disclosure. By behaving inertly it is considered that the gas should not to a major extent participate as a reaction member, and for example, the inert gas should participate as little as possible, such as not participate at all. The performance of the catalyst system was found to be further improved by the addition of hydrogen in the feed diminishing the degree of oligomerization and conversion of ketoacid to undesired components. The hydrogen addition will not introduce hydrogenation activity unless the catalyst system includes a hydrogenation metal but it is proposed to modify the surface properties of the reducible metal oxide which is part of the catalyst system.

The C—C-coupling reactions may be conducted at a flow ratio ($H_2$/liquid feedstock) of, for example, 100-3000 Nl/l, preferably 200-2000 Nl/l, more preferably 500-1800 Nl/l and most preferably 500-1500 Nl/l.

When conducting the reaction in the presence of hydrogen, the catalyst system may include at least one hydrogenation metal in addition to the first and second metal oxides. The hydrogenation metal is for example selected from Group VIII of the Periodic Table of Elements, preferably from Co, Ni, Ru, Rh, Pd, and Pt. A catalyst system including a hydrogenation metal was found to further increase the stability of the catalyst and to suppress the oligomerization reactions to components not suitable for use as fuel components or chemicals.

In another aspect of the present disclosure, a C—C-coupling reaction product obtainable by methods disclosed herein is provided. This product may be directly used as fuel or base oil components or chemicals or as intermediate components in production of fuel or base oil components or chemicals.

The C—C-coupling reaction products obtainable by the methods of the present disclosure may—if desired—be further subjected to hydrodeoxygenation (HDO) to remove oxygen, which for example, produces completely deoxygenated material (i.e. hydrocarbon compounds having no oxygen atoms). The produced hydrocarbons may be used as fuel or base oil components or chemicals or as starting components in the production of fuel or base oil components or chemicals. The hydrodeoxygenated products may also be further isomerized to isoparaffins.

One of the exemplary advantages of the embodiments disclosed herein is that ketoacids produced from renewable materials can be upgraded to higher molecular weight hydrocarbons and/or hydrocarbon derivatives, which may be used as fuel or base oil components or chemicals or as starting components in the production of fuel or base oil components or chemicals.

The C—C-coupling reaction products may be fractionated to remove potential unreacted ketoacid monomers and other low molecular weight components such as water and $CO_2$ formed in the C—C-coupling reactions from the reaction product as illustrated in FIG. 3. The fractionation can be conducted by any known technique such as distillation. The unreacted ketoacid monomer may optionally be recycled and combined with the feed of the first reactor.

Another aspect of the present disclosure involves a method for production of hydrocarbons, an exemplary method including increasing the molecular weight of a ketoacid by using the methods disclosed herein to obtain a C—C-coupling reaction product, and subjecting the C—C-coupling reaction product to hydrodeoxygenation and optionally to an isomerization step.

The HDO catalyst employed in the hydrodeoxygenation may include a hydrogenation metal on a support, such as for example a HDO catalyst selected from a group consisting of Pd, Pt, Ni, Co, Mo, Ru, Rh, W or any combination of these. The hydrodeoxygenation may for example be conducted at a temperature of 100-500° C. and at a pressure of 10-150 bar.

Water and light gases may be separated from the HDO product with any known techniques such as distillation. After the removal of water and light gases the HDO product may be fractionated to one or more fractions suitable for use as gasoline, aviation fuel, diesel or base oil components. The fractionation may be conducted by any known techniques, such as distillation. Optionally part of the product of the HDO step may be recycled and combined to the feed of the HDO reactor.

Another aspect of the present disclosure involves a hydrocarbon composition obtainable by the methods disclosed herein. This product may be used as fuel or base oil components or chemicals or as intermediate components in production of fuel or base oil components or chemicals.

Another aspect of present disclosure involves a hydrocarbon composition having, for example, at least 30 wt-% paraffins, at least 50 wt-% naphthenes, less than 10 wt-% aromatics, and wherein at least 70 wt-% of the hydrocarbons have a carbon number from 8 to 10. This hydrocarbon composition may be obtainable by the methods disclosed herein. This hydrocarbon composition can be used as a gasoline fuel or as gasoline fuel component.

Another aspect of the present disclosure involves a hydrocarbon composition having, for example at least 60 wt-% aliphatic hydrocarbons, at least 30 wt-% aromatics, and wherein at least 70 wt-% of the hydrocarbons have a carbon number from 9 to 24. This hydrocarbon composition may be obtainable by the methods disclosed herein. This hydrocarbon composition can be used as a diesel fuel or as diesel fuel component.

The product of the hydrodeoxygenation step may also be subjected to an isomerization step in the presence of hydrogen and an isomerization catalyst. Both the hydrodeoxygenation step and isomerisation step may be conducted in the same reactor. The isomerisation catalyst may be a noble metal bifunctional catalyst, for example Pt-SAPO or Pt-ZSM-catalyst. The isomerization step may for example be conducted at a temperature of 200-400° C. and at a pressure of 20-150 bar.

It can be preferred that only a part of the HDO product is subjected to an isomerization step, for example, part of HDO product which is subjected to isomerization may be the heavy fraction boiling at or above temperature of 300° C.

The hydrocarbon product obtainable from the hydrodeoxygenation and/or the isomerisation step may be used as fuel or base oil components or chemicals or as intermediate components in production of fuel or base oil components or chemicals.

Generally the choice of subjecting HDO product to isomeration is highly dependable of the desired properties of the end products. In case the HDO product contains a high amount of n-paraffins, the HDO product may be subjected to isomerization step to convert at least part of the n-paraffins to isoparaffins to improve the cold properties of the end product.

EXAMPLES

Materials

As example catalysts, $WO_3/ZrO_2$, $CeO_2/ZrO_2$ and $SiO_2/ZrO_2$ with the compositions presented in Table 1 were used in the C—C-coupling reactions of levulinic acid. The catalysts are available from Saint-Gobain NORPRO.

TABLE 1

| Composition of the catalysts | | | |
|---|---|---|---|
| | $WO_3/ZrO_2$ | $CeO_2/ZrO_2$ | $SiO_2/ZrO_2$ |
| Type | SZ 6*143 | SZ 6*191 | SZ 6*152 |
| Surface Area, m$^2$/g | 130 | 110 | 140 |
| $WO_3$, wt-% | 18 | | |
| $CeO_2$, wt-% | | 18 | |
| $SiO_2$, wt-% | | | 3.3 |
| Atom density | 3.6 W/nm$^2$ | 5.7 Ce/nm$^2$ | 2.4 Si/nm$^2$ |

The weight percentages of the respective oxides are calculated by total mass of the catalyst. The atom densities of the metal of the first metal oxides have been calculated based on the specific surface areas of the catalysts and content of respective metal oxide in the catalyst.

The specific surface areas provided by the catalyst manufacturer have been determined by the BET method, which measures the adsorption isotherm of nitrogen (ASTM D-3663).

Example 1

Increasing the Molecular Weight of Levulinic Acid by C—C Coupling Reactions with $WO_3/ZrO_2$-Catalyst System The performance of $WO_3/ZrO_2$-catalyst (sample SZ 6*143) was evaluated in a continuous tubular flow reactor test run with commercial grade levulinic acid (97%, Sigma-Aldrich) as feedstock.

The C—C coupling reactions were conducted at temperatures ranging from about 200° C. to about 240° C. and under a pressure of about 20 bar, using a weight hourly space velocity (WHSV) of 0.25, 0.5 and 1.0 $h^{-1}$. The reactions were conducted in nitrogen or hydrogen flow (50 ml/min) to study the effect of hydrogen added to the feed. WHSV was calculated from the amount of levulinic acid fed in vessel.

For reactions at various conditions the amount of gas formed was determined from the liquid yield (gas=100–liquid product). The liquid product consists of the organic phase including water formed in the reaction. A rough estimate of the amount of water in liquid product was obtained by thermogravimetric analysis (TGA).

The quantitative amount of LA (levulinic acid) and GVL (γ-valerolactone) in liquid product was determined by HPLC analysis. The relative amount of dimers and oligomers in the organic phase was obtained from GPC chromatograms. The composition of the organic phase, including unreacted LA, was calculated relative to the dry liquid product (without the amount of water).

The product yields and compositions of the organic phase for conversion of levulinic acid on $WO_3/TiO_2$ catalyst system in nitrogen and hydrogen flow are presented in Tables 2 and 3.

TABLE 2

Process conditions and product yields with $WO_3/ZrO_2$-catalyst.

| Process conditions | | | | Product yields | | | |
|---|---|---|---|---|---|---|---|
| Temp. °C. | Pressure bar | Gas flow | WHSV $h^{-1}$ | Gas wt-% | Water wt-% | Organic wt-% | Experiment |
| 200 | 20 | N2 | 0.5 | 0.5 | 3.8 | ~96 | EX 1 |
| 220 | 20 | N2 | 0.5 | 2.3 | 6.2 | ~92 | EX 2 |
| 220 | 20 | N2 | 0.25 | 7.6 | 7.6 | ~85 | EX 3 |
| 240 | 20 | N2 | 0.25 | 8.5 | 12 | ~80 | EX 4 |
| 240 | 20 | N2 | 1.0 | 0.5 | 6.6 | ~93 | EX 5 |
| 220 | 20 | H2 | 0.25 | 1.1 | 8.7 | ~90 | EX 6 |
| 240 | 20 | H2 | 0.25 | 13 | 12 | ~76 | EX 7 |
| 240 | 20 | H2 | 0.25 | 12 | 2.4 | ~86 | EX 8 |

TABLE 3

Product distribution in the organic phase with $WO_3/ZrO_2$-catalyst.

| Composition of organic phase | | | | |
|---|---|---|---|---|
| LA wt-% | GVL wt-% | Dimers wt-% | Oligomers wt-% | Experiment |
| 92 | 0.0 | 8.0 | 0.4 | EX 1 |
| 77 | 0.7 | 19 | 3.1 | EX 2 |
| 58 | 0.3 | 28 | 14 | EX 3 |
| 29 | 0.2 | 30 | 41 | EX 4 |
| 79 | 0.0 | 18 | 3.4 | EX 5 |
| 63 | 0.4 | 28 | 8.4 | EX 6 |
| 40 | 0.9 | 31 | 28 | EX 7 |
| 41 | 0.0 | 35 | 24 | EX 8 |

In EX 8 water was continuously removed from the reaction mixture during the experiment and the amount of water in the product is thus lower than in the other experiments. The product of EX 8 was used as C—C-coupling reaction product feedstock for hydrodeoxygenation experiments in Example 3.

Example 2

Increasing the Molecular Weight of Levulinic Acid by C—C Coupling Reactions with $WO_3/ZrO_2$-, $CeO_2/ZrO_2$- and $SiO_2/ZrO_2$-Catalyst Systems The performance of $WO_3/ZrO_2$-, $CeO_2/ZrO_2$- and $SiO_2/ZrO_2$-catalysts was compared in batch reactor test runs with commercial grade levulinic acid (97%, Sigma Aldrich) as feed. The catalysts were dried at 120° C. in nitrogen flow overnight before being loaded into the reactor. The reactor was loaded with 5 g catalyst and 50 g levulinic acid. The test runs were carried out at 200° C. and 20 bar under nitrogen. Liquid samples withdrawn after 2 hours at 200° C. were analysed for their composition by the GPC method.

TABLE 4

Product distributions in the organic phase

| Catalyst | LA, area-% | Dimers, area-% | Oligomers, area-% |
|---|---|---|---|
| $WO_3/ZrO_2$ | 68 | 26 | 6 |
| $CeO_2/ZrO_2$ | 60 | 31 | 9 |
| $SiO_2/ZrO_2$ | 64 | 30 | 6 |

The contents of Levulinic acid, Dimer and Oligomer in table 4 are based on the peak areas in the GPC chromatogram.

Example 3

Hydrodeoxygenation of the C—C Coupling Reaction Product Fractions to Produce Hydrocarbons In this example, the C—C-coupling reaction product of Experiment 8 in Example 1 was subjected to a hydrodeoxygenation (HDO) step to remove heteroatoms (in particular oxygen) and to stabilize the oil product.

The C—C-coupling reaction product used as feed to the HDO reactor contained 24 wt-% oligomers, 35 wt-% dimers and 41 wt-% of unreacted levulinic acid, which was not removed before feeding to HDO step.

Hydrodeoxygenation was carried out in a tubular flow reactor in presence of sulfided $NiMo/Al_2O_3$ catalyst at temperature of 310° C. and under a pressure of 80 bar using hydrogen to feed (H2/feed) ratio of 3300 Nl/l and weight hourly space velocity (WHSV) of 0.3 $h^{-1}$. WHSV and hydrogen to hydrocarbon ratio is calculated from the amount of tested oil fed in vessel.

The HDO product distribution presented in Table 5 was determined by simulated GC-distillations and the success of oxygen removal was evaluated from FTIR spectra.

The HDO product was distilled into gasoline and diesel fractions. The chemical composition of the gasoline fraction was determined by GC-MS and PIONA analysis. In PIONA analysis compounds present in the sample are quantified and grouped into paraffins, olefins, naphthenes, aromatics and oxygenates. The component analysis is presented as a function of carbon number. For the diesel fraction the amount of aromatics and polar compounds was determined.

TABLE 5

Hydrotreatment product yields.

| Product | Yield, wt-% |
|---|---|
| Water | 31 |
| Gas phase | 35 |
| $CO_2$ (CO) | 11 |
| $C_1$-$C_4$ | 7 |
| $C_5$-$C_9$ | 16 |
| Liquid phase | 35 |
| Gasoline | 7 |
| Diesel | 17 |
| Heavier | 11 |

Unreacted LA present in the HDO feed was partly converted to pentane and this is seen in the relatively high C5-C9 yield in gas phase.

Oxygen can be removed as $H_2O$ in dehydration and HDO reactions, and as $CO_2$ in decarboxylation reactions. The amount of oxygen removed (40 wt-%) corresponds well with the oxygen content in LA (41 wt-%).

The PIONA analysis of the gasoline fraction showed that it contained 37.4 wt-% paraffins (mainly iso-paraffins), 58.2 wt-% naphthenes (mainly paraffinic naphthenes) and 4.1 wt-% aromatics. A small amount of oxygenates (0.2 wt-%) was also observed. The oxygenates were identified to be pentyl ether (0.1 wt-%) and acetone (0.1 wt-%). The compounds of the gasoline fraction are mainly distributed in the C8-C10 range. The carbon content was 85.3 wt-% and hydrogen content 14.6 wt-% corresponding to a molar H/C-ratio of 2.0.

The content of aromatics and polar compounds in the diesel fraction was analysed by HPLC method which showed that the diesel contained 37.6 wt-% aromatics and 0.1 wt-% polar compounds. The remainder (62.3 wt-%) of the diesel fraction was aliphatic hydrocarbons.

The examples show an increase of the molecular weight of levulinic acid by C—C-coupling reactions conducted in the presence of a solid acid catalyst system having a first metal oxide and a second metal oxide. The examples also show that the C—C-coupling reaction product of levulinic acid can be further processed to hydrocarbons having a boiling point range of known components such as gasoline and diesel components by subjecting the C—C-coupling reaction product of levulinic acid to hydrodeoxygenation reactions in the presence of a known HDO catalyst and hydrogen.

The present disclosure relates to catalytic conversion of ketoacids, including methods for increasing the molecular weight of ketoacids, the method including providing in a reactor a feedstock having at least one ketoacid. The feedstock is then subjected to one or more C—C-coupling reaction(s) in the presence of a catalyst system having a first metal oxide and a second metal oxide.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A method for increasing the molecular weight of a ketoacid, the method comprising:
providing in a reactor a feedstock having at least one ketoacid; and
subjecting the feedstock to one or more C—C-coupling reaction(s), wherein the one or more C—C-coupling reaction(s) are conducted in a presence of a solid acid catalyst system having a first metal oxide and a second metal oxide, wherein a content of the at least one ketoacid in the feedstock is at least 30 wt % and the content of water in the feedstock is less than 5.0 wt-%,
wherein the one or more C—C-coupling reaction(s) provides one or more selected from the group consisting of a ketoacid dimer, trimer, tetramer, pentamer, and hexamer, and
wherein the solid acid catalyst system contains the first metal oxide containing tungsten oxide, ceria, or silica supported on a metal oxide carrier, wherein the metal oxide carrier contains the second metal oxide selected from the group consisting of zirconia and titania.

2. The method according to claim 1, wherein the solid acid catalyst system has a specific surface area of from 10 to 500 $m^2$/g.

3. The method according to claim 1, wherein a total amount of the acid sites of the solid acid catalyst system ranges between 30 and 500 µmol/g.

4. The method according to claim 1, wherein the at least one ketoacid is a γ-ketoacid.

5. The method according to claim 1, wherein the content of the at least one ketoacid in the feedstock is at least 40 wt. %.

6. The method according to claim 1, wherein the first metal oxide is supported on the second metal oxide and the surface density of metal atoms of the first metal oxide is from 0.5 to 20 metal atoms/$nm^2$.

7. The method according to claim 1, wherein the content of the first metal oxide in the solid acid catalyst system is 1.0 to 40.0 wt %, calculated by weight of the first metal oxide relative to the total mass of the solid acid catalyst system.

8. The method according to claim 1, wherein the feedstock is introduced into the reactor in liquid phase.

9. The method according to claim 1, wherein the one or more C—C-coupling reaction(s) are conducted at a temperature of 200-400° C.; and/or
wherein the one or more C—C-coupling reaction(s) are conducted at a pressure of 0.5-100 bar; and/or
wherein the one or more C—C-coupling reaction(s) are conducted at a weight hourly space velocity (kg feedstock/kg solid acid catalyst*h) of 0.05 $h^{-1}$ to 2.0 $h^{-1}$.

10. The method according to claim 1, wherein the one or more C–C-coupling reaction(s) are conducted in the presence of hydrogen, wherein the feedstock is introduced into the reactor in liquid phase and the one or more C–C-coupling reaction(s) are conducted at a hydrogen feed ratio ($H_2$/liquid feedstock) of 100-3000 Nl/l, and/or wherein the solid acid catalyst system comprises:
at least one hydrogenation metal selected from Group VIII of the Periodic Table of Elements.

11. A method for producing hydrocarbons by increasing a molecular weight of a ketoacid to obtain a C—C-coupling reaction product, the method comprising:
providing in a reactor a feedstock having at least one ketoacid;
subjecting the feedstock to one or more C—C-coupling reaction(s),
wherein the one or more C—C-coupling reaction(s) are conducted in a presence of a solid acid catalyst system having a first metal oxide and a second metal oxide, and
wherein a content of the at least one ketoacid in the feedstock is at least 30 wt % and the content of water in the feedstock is less than 5.0 wt-%;

subjecting the C—C-coupling reaction product to hydrodeoxygenation, wherein the one or more C—C-coupling reaction(s) provides one or more selected from the group consisting of a ketoacid dimer, trimer, tetramer, pentamer, and hexamer, and wherein the solid acid catalyst system contains the first metal oxide containing tungsten oxide, ceria, or silica supported on a metal oxide carrier, wherein the metal oxide carrier contains the second metal oxide selected from the group consisting of zirconia and titania.

12. The method according to claim 1, wherein the at least one ketoacid is levulinic acid.

13. The method according to claim 1, wherein the content of the at least one ketoacid in the feedstock is at least 50 wt-%, and/or the content of water in the feedstock is less than 2.0 wt-%.

14. The method according to claim 1, wherein the content of the at least one ketoacid in the feedstock is at least 90 wt-%, and/or the content of water in the feedstock is 1.0 wt-%.

15. The method according to claim 1, wherein the content of the at least one ketoacid in the feedstock is at least 95 wt-%, and/or the content of water in the feedstock is 1.0 wt-%.

16. The method according to claim 1, wherein the content of the first metal oxide in the solid acid catalyst system is 2.0 to 30.0 wt-%, calculated by weight of the first metal oxide relative to the total mass of the solid acid catalyst system.

17. The method according to claim 1, wherein the content of the first metal oxide in the solid acid catalyst system is 13.0 to 30.0 wt-%, calculated by weight of the first metal oxide relative to the total mass of the solid acid catalyst system.

18. The method according to claim 1, wherein the one or more C—C-coupling reaction(s) are conducted at a temperature of 210-300° C.; and/or
wherein the one or more C—C-coupling reaction(s) are conducted at a pressure of 1.0-50 bar; and/or
wherein the one or more C—C-coupling reaction(s) are conducted at a weight hourly space velocity (kg feedstock/kg solid acid catalyst system*h) of 0.1 $h^{-1}$ to 1.8 $h^{-1}$.

19. The method according to claim 1, wherein the one or more C—C-coupling reaction(s) are conducted at a temperature of 220-280° C.; and/or
wherein the one or more C—C-coupling reaction(s) are conducted at a pressure of 1.0-20 bar; and/or
wherein the one or more C—C-coupling reaction(s) are conducted at a weight hourly space velocity (kg feedstock/kg solid acid catalyst system*h) of 0.2 $h^{-1}$ to 1.5 $h^{-1}$.

20. The method according to claim 1, wherein the one or more C—C-coupling reaction(s) are conducted at a temperature of 220-260° C.; and/or
wherein the one or more C—C-coupling reaction(s) are conducted at a pressure of 1.0-20 bar; and/or
wherein the one or more C—C-coupling reaction(s) are conducted at a weight hourly space velocity (kg feedstock/kg solid acid catalyst system*h) of 0.25 $h^{-1}$ to 1.25 $h^{-1}$.

21. The method according to claim 1, wherein the one or more C—C-coupling reaction(s) are conducted in the presence of hydrogen, wherein the feedstock is introduced into the reactor in liquid phase and the one or more C—C-coupling reaction(s) are conducted at a hydrogen feed ratio ($H_2$/liquid feedstock) of 200-2000 Nl/l, and/or wherein the solid acid catalyst system comprises:
at least one hydrogenation metal selected from Group VIII of the Periodic Table of Elements.

22. The method according to claim 1, wherein the feedstock is introduced into the reactor in liquid phase and the one or more C—C-coupling reaction(s) are conducted in the presence of hydrogen, wherein the one or more C—C-coupling reaction(s) are conducted at a hydrogen feed ratio ($H_2$/liquid feedstock) of 500-1800 Nl/l, and/or wherein the solid acid catalyst system comprises:
at least one hydrogenation metal selected from Group VIII of the Periodic Table of Elements.

23. The method according to claim 1, wherein the feedstock is introduced into the reactor in liquid phase and the one or more C—C-coupling reaction(s) are conducted in the presence of hydrogen, wherein the one or more C—C-coupling reaction(s) are conducted at a hydrogen feed ratio ($H_2$/liquid feedstock) of 500-1500 Nl/l, and/or wherein the solid acid catalyst system comprises:
at least one hydrogenation metal selected from Group VIII of the Periodic Table of Elements.

24. The method according to claim 21, wherein the at least one hydrogenation metal includes at least one of Co, Ni, Ru, Rh, Pd, and Pt.

25. The method according to claim 22, wherein the at least one hydrogenation metal includes at least one of Co, Ni, Ru, Rh, Pd, and Pt.

26. The method according to claim 23, wherein the at least one hydrogenation metal includes at least one of Co, Ni, Ru, Rh, Pd, and Pt.

* * * * *